(12) United States Patent
Borodic (10) Patent No.: US 7,537,773 B1
(45) Date of Patent: May 26, 2009

(54) CHEMODENERVATING PHARMACEUTICAL AS ANTI-INFLAMMATORY AGENT

(75) Inventor: Gary E. Borodic, Canton, MA (US)

(73) Assignee: Botulinum Toxin Research Associates, Inc., Quincy, MA (US)

( * ) Notice: Subject to any disclaimer, the term of this patent is extended or adjusted under 35 U.S.C. 154(b) by 887 days.

(21) Appl. No.: 09/382,837

(22) Filed: Aug. 25, 1999

Related U.S. Application Data (60) Provisional application No. 60/097,846, filed on Aug. 25, 1998.

(51) Int. Cl.
*A61K 45/00* (2006.01)
*A61K 47/00* (2006.01)

(52) U.S. Cl. .................... 424/282.1; 424/278.1

(58) Field of Classification Search ............ 424/282.1; 514/886, 929, 825
See application file for complete search history.

(56) References Cited

U.S. PATENT DOCUMENTS

| | | | |
|---|---|---|---|
| 5,053,005 | A | 10/1991 | Borodic |
| 5,183,462 | A | 2/1993 | Borodic |
| 5,298,019 | A | 3/1994 | Borodic |
| 5,401,243 | A | 3/1995 | Borodic |
| 5,437,291 | A * | 8/1995 | Pasricha et al. ............. 128/898 |
| 5,512,547 | A | 4/1996 | Johnson et al. |
| 5,562,907 | A | 10/1996 | Arnon |
| 5,670,484 | A | 9/1997 | Binder |
| 5,674,205 | A | 10/1997 | Pasricha et al. |
| 5,696,077 | A | 12/1997 | Johnson et al. |
| 5,714,468 | A | 2/1998 | Binder |
| 5,837,265 | A | 11/1998 | Montal et al. |
| 5,846,929 | A | 12/1998 | Johnson et al. |
| 6,063,768 | A | 5/2000 | First |
| 6,113,915 | A | 9/2000 | Aoki et al. |
| 6,159,944 | A * | 12/2000 | Fogel |
| 6,458,365 | B1 | 10/2002 | Aoki et al. |
| 2003/0138437 | A1 | 7/2003 | Hunt |
| 2004/0126396 | A1 | 7/2004 | Aoki et al. |

FOREIGN PATENT DOCUMENTS

WO    WO 95/28171    10/1995

OTHER PUBLICATIONS

The Merck Manual 16th ed., Berkow, ed. pp. 318-320, 1308-1311, 2368, 1992.*
Scholzen, T et al. Exp Dermatol 7:81-96, 1998.*
Merayo-Lloves J, Calonge M, Foster CS Experimental model of allergic conjunctivitis to ragweed in guinea pig Curr. Eye Research 14:487-494, 1995.
Jankovic J, Brin M Therapeutic uses of botulinum toxin 1991, NEJM 324:1186-1194.
Bushara Ko, Park DM Botulinum toxin and sweating J Neurol, Neurosurg., Psychtr. 1994: 57(11), 1437-1438.
Parricha PJ, Ravich WJ, Hendrix TR, Sostre S, Jones B, Kallo AN Intrasphincteric Botulinum toxin for the treatment of achalasia NEJM 1995: 332,774-778.
Bottinger H, Reuner KH, Aktories K Inhibition of histamine release from rat mast cells by botulinum C2 toxin. Int Arch Allergy Appl Immunol 84:380-384, 1987.
Acquadro, M., et al., Treatment of myofascial pain with botulinum A toxin, *Anesthesiology* Mar. 1994; 80(3):705-6.
Amann, R., et al., Intraplantar injection of nerve growth factor into the rat hind paw: local edema and effects on the termal nocieptive threshol, *Pain 1995*; 64:323-329.
Ashikaga, T., et al., Multiple daily insulin injections in the treatment of diabetic retinopathy, The Job Study Revisited, *Diabetes* May 1978; 27(5):592-6.
Bischoff, S.C., et al., Effect of Nerve Growth Factor on the Release of Inflammatory Mediators by Mature Human Basophils, *Blood* May 15, 1992; 79(10):2663-2669.
Borodic, G., Myasthenic crisis after botulinum toxin. *Lancet* Dec. 5, 1998); 352(9143):1832.
Borodic, G, et al., Botulinum toxin therapy, immunologic resistance, and problems with available materials, *Neurology* Jan. 1996; 46(1):26-9.
Borodic, G., et al., Antibodies to botulinum toxin, *Neurology* Jan. 1995; 45(1):204.
Borodic, G., Therapeutic botulinum toxin, *Lancet* Nov. 12, 1994; 344(8933):1370.
Borodic, G., et al., New concepts in botulinum toxin therapy, *Drug Saf* Sep. 1994; 11(3):145-52.
Borodic, G., et al., Antibodies to Botulinum toxin, *Ophthalmology* Jul. 1994; 11(3):1158-9.
Borodic, G., et al., Histologic assessment of dose-related diffusion and muscle fiber response after therapeutic botulinum A toxin injections, *Movement Disorders 1994*; 9(1):31-9.
Borodic, G., et al., Botulinum B toxin as an alternative to botulinum A toxin: a histologic study, *Ophthal Plast Reconstr Surg 1993*; 9(3):182-90.
Borodic, G., et al. Contralateral injections of botulinum A toxin for the treatment of hemifacial spasm to achieve increased facial symmetry, *Plast Reconstr Surg* Dec. 1992; 90(6):972-7.
Borodic, G., et al. Effects of repeated botulinum toxin injections on orbicularis oculi muscle, *J Clin Neuroophthalmol* Jun. 1992; 12(2):121-7.

(Continued)

*Primary Examiner*—G. R Ewoldt
(74) *Attorney, Agent, or Firm*—Milbank, Tweed, Hadley & McCloy, LLP (57) ABSTRACT

Pharmaceutical application of a chemodenervating agent, particularly botulinum toxin, reduces inflammatory response and serves as an anti-inflammatory agent without systemic side effects and with long duration action, on the order of 12-24 weeks. In one embodiment, the effective dosage for allergy provoked inflammation reduction is an order of magnitude less than dosages associated with treatment of regional movement diseases, since the agent works to reduce inflammation by reducing histamine and other preformed mediator releases associated with mast cell degranulation.

24 Claims, 9 Drawing Sheets

(9 of 9 Drawing Sheet(s) Filed in Color)

OTHER PUBLICATIONS

Borodic, G., et al. Botulinum A toxin for spasmodic torticollis: multiple vs single injection points per muscle, *Head Neck* Jan.-Feb. 1992; 14(1):33-7.

Borodic, G., et al. Treatment of spasticity with botulinum toxin, *Ann Neurol* Jan. 1992; 31(1):113.

Borodic, G., Botulinum A toxin for (expressionistic) ptosis overcorrection after frontalis sling, *Ophthal Plast Reconstr Surg* 1992; 8(2):137-42.

Borodic, G., et al. Botulinum A toxin for the treatment of adult-onset spasmodic torticollis, *Plast Reconstr Surg* Feb. 1991; 87(2):285-9.

Borodic, G., et al. Innervation zone of orbicularis oculi muscle and implications for botulinum A toxin therapy, *Ophthal Plast Reconstr Surg* 1991; 7(1): 54-60.

Borodic, G., et al. Botulinum A toxin for the treatment of spasmodic torticollis dysphagia and regional toxin spread, *Head Neck* Sep.-Oct. 1990; 12(5):392-9.

Borodic, G., et al. Blepharospasm and its treatment, with emphasis on the use of botulinum toxin, *Plast Reconstr Surg* Mar. 1989; 83(3):546-54.

Borodic, G., et al. Dermis fat graft in eviscerated sockets, *Ophthal Plast Reconstr Surg* 1989; 5(2):144-9.

Borodic, G., et al. Immunoglobulin deposition in localized conjunctival amyloidosis, *Am J Ophthalmol* Nov. 1984; 98(5):617-22.

Borodic, G., et al. Therapeutic botulinum toxin: histologic effects and diffusion properties, *DasGupta BR, ed Botulinum and Tetanus Neurotoxins*. Plenum Press, New York 1993, 623-45.

Borodic, G., Botulinum toxin: issues and applications, *Otolaryngology Head Neck Surg* 1999; 7:219-25.

Bottinger, H., et al., Inhibition of histamine release from rat mast cells by botulinum C2 toxin, *Int Arch Allergy Appl Immunol* 1987; 84(4):380-4.

Brooks, A., et al., Reactive oxygen species generation and histamine release by activated mast cells: modulation by nitric oxide synthase inhibition, *Br J Pharmacol* 1999; 128:585-90.

Calderone, J., et al., Intraocular pathology of trisomy 18 (Edwards's syndrome): report if a case and review of the literature, *Br J Ophthalmol* Mar. 1983; 67(3):162-9.

Chen, X., et al., NOS Inhibitor antagonism of $PGE_2$-induced mechanical sensitization of cutaneous C-fiber nociceptors in the rat, *Am Psych Soc* 1999; 963-6.

Dines, K., et al., Mast cell interactions with the nervous system: relationship to mechanisms of disease, *J Neuropathol Exp Neurol* 1997, 56(6):627-40.

Fujishima, H., et al., Elevated levels of substance P in tears of patients with allergic conjunctivitis and vernal keratoconjunctivitis, *Clin Exp Allergy* 1997; 27:372-8.

First, E., et al., Dose standardization of botulinum toxin, *Lancet* Apr. 23, 1994; 343(8904):1035.

Hayashi, N., et al., Giant cell angiofibroma of the orbit and eyelid, *Ophthalmology* Jun. 1999; 106(6):1223-9.

Jensen, W., et al., The susceptibility of the mallard duck (Anas platyrhynchos) to Clostridium botulinum C2 toxin, *Jpn J Med Sci Biol* Mar. 1980; 33(2):81-6.

Just, I., et al., ADP-ribosylation of Drosophila indirect-flight-muscle actin and arthrin by Clostridium botulinum C2 toxin and Clostridium perfringens iota toxin, *Biochem J* Apr. 1993; 291 (Pt 2):409-12.

Kinde, H., et al., Clostridium botulinum type-C intoxication associated with consumption of processed alfalfa hay cubes in horses, *J Am Vet Med Assoc* Sep. 15, 1991; 199(6):742-6.

Lambiase, A., et al., Increase plasma levels of substance P in vernal keratoconjunctivitis, *Invest Ophthalmol Vis Sci* Sep. 1997; 30(10):2161-4.

Lambiase, A., et al., Expression of nerve growth factor receptors on the ocular surface in healthy subjects and during manifestation of inflammatory diseases, *IOVS* Jun. 1998; 38(7):1272-5.

Leon, A., et al., Mast cells synthesize, store, and release nerve growth factor, *Proc Natl Acad Sci* Apr. 1994; 91 3739-43.

Levi-Montalcini, R., et al., Update of the NGF saga, *J Neurol Sci* 1995; 130:119-127.

Levi-Montalcini, R., et al., Nerve growth factor: from neurotrophin to neurokine, *TINS* 1996; 19(11):514-20.

Lewin, G., et al., Nerve Growth Factor and nociception, *TINS* 1993; 16(9):353-9.

Matter, K., et al., Actin involvement in exocytosis from PC12 cells: studies on the influence of botulinum C2 toxin on stimulated noradreneline release, *J Neurochem*, Feb. 1989; 52(2):370-6.

Mauss, S., et al., Inhibition of the contraction of the isolated longitudinal muscle of the guinea-pig ileum by botulinum C2 toxin: evidence for a role of G/F-actin transition in smooth muscle contraction, *Naunyn Schmiedebergs Arch Pharmacol* Sep. 1989; 340(3):345-51.

Mendell, L., et al., Neurotrophins, nociceptors, and pain, *Microscopy Res Technique* 1999; 45:252-61.

Nakamura, S., et al., C2 toxin production by Clostridium botulinum type C strains producing no C1 toxin, *Jpn J Med Sci Biol* Apr. 1979; 32(2):128-9.

Nakamura, S., et al., Sporulation and C2 toxin production by Clostridium botulinum type C strains producing no C1 toxin, *Microbial Immunol* 1978; 22(10):591-6.

Ohishi, I., et al., Histopathological effect of botulinum C2 toxin on mouse intestines, *Infect Immun* Jan. 1984; 43(1): 54-8.

Pearce, L., et al., Pharmacologic characterization of botulinum toxin for basic science and medicine, *Toxicon* Sep. 1997; 35(9):1373-412.

Pearce, L., et al., Botulinum toxin: death versus localized denervation, *J R Soc Med* Apr. 1995; 88(4):239-40.

Pearce, L., et al., The median paralysis unit: a more pharmacologically relevant unit of biologic activity for botulinum toxin, *Toxicon* Feb. 1995; 33(2):217-27.

Pearce, L., et al., Measurement of botulinum toxin activity: evaluation of the lethality assay, *Toxicol Appl Pharmacol* Sep. 1994; 128(1):69-77.

Pearce, L., et al., Botulinum toxin potency: a mystery resolved by the median paralysis, *J R Soc Med* Sep. 1994; 87(9):571-2.

Ritter, A., et al., Regulation of myelinated nociceptor function by nerve growth factor in neonatal and adult rats, *Br Res Bul* 1993; 30:245-49.

Sanico, A., et al., Nerve growth factor expression and release in allergic inflammatory disease of the upper airways, *Am J Respir Crit Care Med* 2000; 161:1631-5.

Simpson, L., A comparison of the pharmacological properties of Clostridium botulinum type C1 and C2 toxins, *J Pharmacol Exp Ther* Dec. 1982; 223(3):695-701.

Simpson, L., Molecular basis for the pharmacological actions of Clostridium botulinum type C2 toxin, *J Pharmacol Exp Ther* Sep. 1984; 230(3):665-9.

Tarsy, D., et al., Myasthenia gravis after botulinum toxin A for Meige syndrome, *Mov Disord* Jul. 2000; 15(4):736-8.

Troll, G., et al., Diplopia after cataract surgery using 4% lidocaine in the absence of Wydase, *J Clin Anesth* Nov. 1999; 11(7):615-6.

Woolf, C., et al., Peripheral cell types contributing to the hyperalgesic action of nerve growth factor in inflammation, *J Neurosc* Apr. 15, 1996; 16(8): 2716-23.

Yamaji, M., et al., Role of substance P in experimental allergic conjunctivitis in guinea pigs, *Meth Find Exp Clin Pharmaco* 1997; 19(9):637-43.

Buzzi, M.G., et al., Neurogenic model of migraine, *Cephalalgia* 1995; 15(4):277-80.

Moskowitz, M.A., et al., Neuroeffector functions of sensory fibres: implications for headache mechanisms and drug actions, *J Neurol* 1991; 238 Suppl 1:S18-22.

Soter, N.A., et al., Release of mast-cell mediators and alterations in lung function in patients with cholinergic urticaria, *N Engl J Med* Mar. 13, 1980; 302(11):604-8.

Levine, J.D., et al., Intraneuronal substance P contributes to the severity of experimental arthritis, *Science* 1984 No. 2; 226(4674):547-9.

Lassen, L.H., et al., Histamine induces migraine via the H1-receptor. Supoort for the NO hypothesis of migraine, *Neuroreport* Jul. 31, 1995; 6(11):1475-9.

Buzzi, M.G., et al., 5-Hydroxytryptamine receptor agonists for the abortive treatment of vascular headaches block mast cell, endothelial and platelet activation within the rat dura mater after trigeminal stimulation, *Brain Res* Jun. 26, 1992; 583(1-2):137-49.

Dimitriadou, V., et al., Ultrastructural evidence for neurogenically mediated changes in blood vessels of the rat dura mater and tongue following antidromic trigeminal stimulation, *Neuroscience* 1992; 48(1):187-203.

Dimitradou, V., et al., Trigeminal sensory fiber stimulation induces morphological changes reflecting secretion in rat dura mater mast cells, *Neuroscience* 1991; 44(1):97-112.

Kokumai, S., et al., Effect of a capsaicin as a neuropeptide-releasing substance on sneezing reflex in a type I allergic animal model, *Int Arch Allergy Immunol* 1992; 98(3):256-61.

Takeda, N., et al., Neurogenic inflammation in nasal allergy: histochemical and pharmacological studies in guinea pigs. A review, *Acta Otolaryngol Suppl* 1993; 501:21-4.

Kellogg, D.L., et al,. Cutaneous active vasodilation in humans is mediated by cholinergic nerve cotransmission, *Circ Res* Dec. 1995; 776(6):1222-8.

Meijer, F., et al., Nitric oxide plays a role as mediator of conjunctival edema in experimental allergic conjunctivitis, *Exp Eye Res* Apr. 1996; 62(4):359-65.

Wang, Z.Y., et al., The contribution of nitric oxide to endotoxin-induced ocular inflammation: interaction with sensory nerve fibres, *Br J Pharmacol* Jul. 1996; 118(6):1537-43.

Monteforte et al. "Morphological changes in from mast cells induced by nerve stimulation in vivo," Neuroscience Letters 315 (2001) 77-80.

Jasmin et al. "CNS induced neurogenic cystitis is associated with bladder mast cell degranulation in the rat," American Urological Association, Inc., vol. 164, 852-855, Sep. 2000.

Mio et al. "Substance P-induced histamine release from rat peritoneal mast cells and its inhibition by antiallergic agents and calmodulin inhibitors," Immunopharmacology, 22 (1991) 59-66.

Dimitriadou et al. "Trigeminal sensory fiber stimulation induces morphological changes reflecting secretion in rat dura mater mast cells," Neuroscience, vol. 44, No. 1, pp. 97-112, 1991.

Coderre et al. "Neural control of vascular permeability: Interactions between primary afferents, mast cells, and sympathetic efferents," Journal of Neurophysiology, vol. 62, No. 1, Jul. 1989.

* cited by examiner

CHEMODENERVATING PHARMACEUTICAL AS ANTI-INFLAMMATORY AGENT

This application claims the benefit of U.S. Provisional Application Ser. No. 60/097,846, filed Aug. 25, 1998. U.S. Provisional Application Ser. No. 60/097,846, filed Aug. 25, 1998, is hereby incorporated herein in its entirety.

FIELD OF INVENTION

This invention relates to the use of chemodenervating agents in the treatment of disease, and more particularly to its use as an anti-inflammatory agent.

BACKGROUND OF THE INVENTION

Immunity and inflammation are forms of physiologic processes defined as the body's response against foreign substances such as antigens or, in some cases, itself, autoantigens, or some form of damaging biologic or mechanical insult. The process often involves the production of antibodies by type B lymphocytes which interact with foreign substances and subsequently destroy or inactivate the antigen using a number of cellular and chemical amplification systems and regulation systems such as complement, arachadonic acid metabolites such as prostaglandin and leukotriennes, cytokines, preformed mediators such as serotonin and histamine, and enzymes. Inflammatory responses occur in conjunction and as a result of the immune recognition process and functions to provide the basic tissue insult.

Unfortunately, inflammatory reactions intrinsically may have destructive effects on tissue and organ structure and function, and may lead to painful or subjectively adverse sensory experiences. A specific form of inflammation defined herein deals with an organism's ability to produce a rapid regional inflammatory response over a several second to 12 hour period.

While various anti-inflammatory agents have existed in the past, none have been associated with the mechanism of regional chemodenervation such as achievable with botulinum toxin. Regional chemodenervation refers to the practice of injecting or otherwise providing the chemodenervation agent to a particular-region or site with diffusion of that agent from that site over a fixed distance. Dosages associated with regional chemodenervation range from 20-600 units per region for the treatment of movement disease.

Regional chemodenervation is accomplished for therapeutic purposes for the treatment of a number of movement disorders of the body, involving excessive tone, involuntary movement and abnormal postures often associated with abnormal sensations. Examples of such movement disorders include essential blepharospasm, hemifacial spasm, adult onset spasmodic torticollis, regional occupation limb and hand dystonia, spasmodic dysphonia, aberrant facial nerve region with facial muscle synkinesis, and bruxism and jaw dystonia as described by Borodic, G. E., Pearce, L. B., Johnson, E., Schantz, E., Clinical and Scientific Aspects of Therapeutic Botulinum toxin Administrations, Opthalmology Clinics of N. America, September, Vol. 4, No. 3, 1991.

Chemodenervation is accomplished by injecting a biologically quantized amount of botulinum toxin into the regional muscles involved with the involuntary movement, effecting a block in neuromuscular transmission leading over a period of several weeks to neurogenic muscular atrophy, decreased muscular resting tone and decreased muscular contractility over a defined region determined by the quantity of chemodenervating agent used in the injection site. The preferred agent is botulinum toxin, generally quantized using the LD 50 bioassays which may be refined by regional denervation bioassays as described by Borodic, G. E., Alderson, K., Pearce, L. B., Ferrante, R., Histologic changes in muscle and clinicopathologic correlations after therapeutic botulinum toxin administration, Textbook of Botulinum toxin Therapy Eds, J. Jankovic, M. Hallet, M. Dekker, New York, Hong Kong, Chapter 10, Pages 119-158, 1994.

The botulinum unit is defined as that quantity of botulinum toxin capable of killing 50% of a population of Swiss Webster mice. The quantity is an activity unit, and specifically not a unit of mass. Depending on the quality of the botulinum toxin used, the mass necessary to produce this activity may vary.

The dosage associated with such regional movement diseases is on the order of 25-600 units, with the duration of the chemodenervative effect being generally 12-16 weeks, with complete reversibility for most therapeutic preparations of botulinum toxin. Botulinum is known to exist as immunotypes A-G which affect different cytoplasmic acceptor proteins after being internalized at the presynaptic motor axon terminal. Each immunotype has been associated with varying durations of action and chemodenervating potency per LD 50 unit, as described by Borodic, G. E., Pearce, L. B., New Concepts in Botulinum toxin Therapy, Drug Safety 11(3): 145-152, 1994.

Despite the known tissue effects from regional injections of botulinum toxin, certain medical observations regarding the use of chemodenervating agents can not be easily explained by such denervating tissue effects. For instance, when chemodenervation is used to treat patients with benign essential blepharospasm, photophobia or sensitivity of the eye to light is often markedly decreased. Botulinum toxin in the dosages associated with the blocking in neuromuscular transmissions has also been shown to occasionally be helpful for the treatment of regional pain syndromes such as myofascial pain syndromes, headaches, and migraine headaches which can not easily be explained by the traditional chemodenervation model that has been evoked for the efficacy in regional movement diseases.

SUMMARY OF THE INVENTION

It has been found that the use of botulinum toxin in doses from ⅓rd to several orders of magnitude less than those associated with treatment of regional movement diseases has been effective to reduce inflammation and adverse sensory experiences associated with the inflammatory response. These observations are explained by the fact that it has been found that low dosages of the subject chemodenervative agent reduces histamine releases and releases of other preformed mediators associated with mast cell degranulation. The subject bioeffect is noted at low dosages of the chemodenervative agent in one animal model of ocular surface disease well noted for histamine release and releases of other preformed mediators associated with mast cell degranulation and rapid inflammatory response.

It is a finding of the subject invention that chemodenervative pharmaceuticals such as botulinum toxin in low dosages are effective anti-inflammatory agents. Typical minimum effective doses range from 0.5-5 units as opposed to 20-600 units used for treatment of movement disorders. This is because the low dosages regionally block rapid tissue responses characteristic of inflammation within a defined geometric diffusion field in which this chemodenervating agent is known to exert its effect. Within this defined area, low dosages of botulinum toxin are demonstrated to block edema, erythema, abnormal sensory experiences, and heat transfer, occurring rapidly over a predefined region.

This new bioeffect of anti-inflammatory action is explained by the resultant blockage of mast and nerve cell release of histamine and other preformed mediators which result in vascular dialation, increased permeability, altered sensory experience, edema and erythema. It is thus a finding of this invention that inflammation is inhibited by administration of the subject chemodenervative agent.

For instance, chemodenervative pharmaceuticals such as botulinum toxin have been found in low dosages to block the medical condition known as cholinergic urticaria. Hive formation or urticaria, may also be treated with such low dosages, as mast cell release of histamine and other preformed mediators which result in vascular dialation, increased permeability, edema and erythema is inhibited by administration of the subject chemodenervative agent.

It is a finding of the subject invention that inflammation is reduced because mast cell release of histamine and other preformed mediators is reduced, making this anti-inflammatory agent useful in treating a number of diseases in which inflammation comprises a basic mechanism or a major component. For instance, inflammation associated with allergic blepharoconjunctivitis, giant papillary conjuctivitis, hayfever, and uveitis, eg. internal ocular inflammation, are treatable with the chemodenervating agent. The inflammatory components associated with the diagnosis of rheumatoid arthritis, Crohn's disease and ulcerative colitis are also conditions capable of responding to treatment by the subject anti-inflammatory agent.

The subject anti-inflammatory agent's unique property relates to suppression of the component for the inflammatory response which occurs rapidly, and which is mediated by neural reflex mechanisms.

It has been found that Type 1 hypersensitivity reactions are reduced with the subject anti-inflammatory agent. Such hypersensitivity reactions are classic for rapid expression of the inflammatory response often leading to edema with increased vascular permeability, erythema, abnormal sensory experiences, and increased heat release.

Additionally, it has been found that the subject anti-inflammatory agent relieves photophobia in essential blepharospasm. Photophobia is a hallmark symptom of ocular inflammation. Moreover, it has been found that the subject anti-inflammatory agent reduces anal fissures in response to perirectal botulinum toxin administration.

Mast Cells

It will be appreciated that mast cells are known to contain a number of substances important to inflammatory responses in hypersensitivity reactions, and substantially participate in more generalized inflammatory reactions. The mast cell is abundantly found in pathologic tissue specimens in patients with rheumatoid arthritis, inflammatory bowel disease, certain forms of ocular uveitis, eczema, and asthma.

Mast cell activation has been associated with the production of both preformed mediators such as histamine, newly formed mediators such as leukotriennes and prostaglandins, cytokines, including interleukin-5, interleukin-8, kininogenase, and platelet activating factor. A number of these mast cell constituents play a role in the inflammatory response functioning as chemoattractants, activators and spasmogens. Additionally, a number of these constituents are activated and released in response to neural stimulation and play a role in neural sensory adaptation systems. Histamine is well known to produce itching sensation causing a compulsion to scratch or stimulate the activated area. Histamine also causes pain in patients with genetic predisposition to develop essential headaches.

An especially important cytokine identified as being important to inflammation and pain is tumor necrosis factor alpha. Tumor necrosis factor alpha has been identified in activated mast cells, and plays a role in modulation of mast cell activity as described by Cocchiara, R., et al, Histamine and Tumor Necrosis Factor-alpha Production from Purified Rat Brain Mast Cells Mediated by Substance P. Neuroreport 1999 Feb. 25; 10(3):575-8, and Olejnik, A. K., Brzezinska-Blaszczyk, E., Tumor Necrosis Factor Alpha (TNF-alpha) Modulates Rat Mast Cell Reactivity, Immunol Lett 1998 December; 64 (2-3): 167-71, Tumor Necrosis Factor has been Isolated from Diseased Tissues known to have Considerable Mast Cell Presence and Reactivity, Ackermann, L., Harvima, I. T., Mast Cells of Psoriatic and Atopic Dermatitis Skin are Positive for TNF-alpha and their Degranulation is Associated with Expression of ICAM-1 in the Epidermis, Arch Dermatol Res 1998 July; 290(7):353-9; and Furuta, G. T., et al. Mast Cell-Dependent Tumor Necrosis Factor Alpha Production Participates in Allergic Gastric Inflammation in Mice, Gastroenterology 1997 November; 113(5): 1560-9.

Anti-tumor necrosis factor, as well as other formed and newly formed mediators are autocoids which are reduced when suppressing mast cell releases induced by botulinum toxin in low-level dosages.

Thus, the subject denervating agent, e.g. botulinum toxin, is demonstrated to achieve a reduction in rapid phase inflammatory responses. The responses are under neural regulation, involving mast cells degranulating autocoid releases activated by either non-immunologic or immunologic-based processes.

Although botulinum toxin Type A is the currently preferred chemodenervating agent, other immunotypes of botulinum toxin Type B-G may be substituted based on demonstrated anti-inflammatory efficacy.

In summary, pharmaceutical application of a chemodenervating agent, particularly botulinum toxin, reduces inflammatory response and serves as an anti-inflammatory agent without systemic side effects and with long duration action, on the order of 12-24 weeks. In one embodiment, the effective dosage for allergy provoked inflammation reduction is an order of magnitude less than dosages associated with treatment of regional movement diseases, since the agent works to reduce inflammation by reducing histamine and other preformed mediator releases associated with mast cell degranulation. The effects recognized herein give new utility to chemodenervating agents.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

These and other features of the subject invention will be better understood in connection with the Detailed Description taken in conjunction with the Drawings, of which.

DETAILED DESCRIPTION

In the subject invention, a chemodenervative agent is given in a therapeutically effective dose to reduce inflammation, and may be used in any application in which inflammation is present or to augment other inflammatory agents. The administration may be by injection, topical application, or other means to assure a therapeutically effective dose delivered to the site. Not only is the subject treatment efficacious in disease treatment normally associated with the occurrence of inflammation, it is also efficacious in the treatment of other diseases. Note that mechanical or adjuvant chemical activity may be necessary to increase penetration by topical application.

The efficacy of botulinum toxin to treat inflammation is demonstrated in the following examples:

Uticaria

Case I

A 53-year-old woman had a history of Bell's Palsy five years prior to being evaluated for asymmetric facial movements from synkinesis. The facial movements were causing involuntary eyelid closure. Additionally, she noted abnormality in forehead creases and desired achieving facial forehead crease wrinkle symmetry by injection of botulinum into the frontalis muscle. After exercising, she noted that she would traditionally break out in hives, eg. urticaria, throughout her body, with the facial region being most severely involved. This urticarial reaction was closely associated with itching.

Two weeks after botulinum toxin injection at a dose of 2.5 units per injection site, an unusual phenomenon was noted on her forehead after exercising. An area measuring three to four centimeters around each injection area was protected from hive, itching or erythema. Other areas of the face were involved in the usual hive, erythema and flushing reaction experienced with exercising. The protective area phenomena could be seen to be concentrated around each injection site, and could be observed after each period of exercise for about 10 to 14 weeks after which the protected area could no longer be demonstrated.

Figure 1:
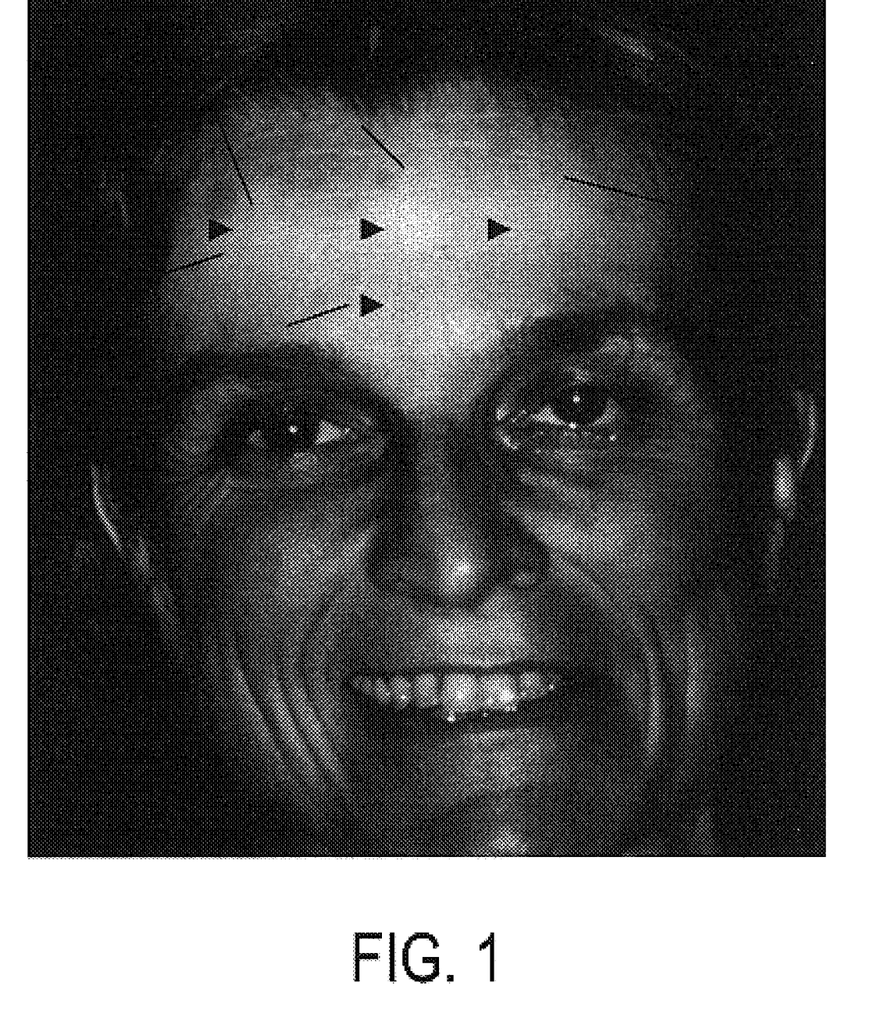
FIG. 1 is a photograph showing the results of the injection of a chemodenervating agent at various injection sites on the forehead of a patient suffering from flushing and urticaria after exertion, showing a reduction in inflammatory reaction-around the injection sites in a geometric field precisely corresponding to the diffusion field for the injected dose of botulinum toxin.

As can be seen by the photograph of FIG. 1, the effect detected by the use of red sensitive Kodachrome film-™ is demonstrated. Here, the arrow heads denote where botulinum toxin was injected, with the lines denoting the area where reactive vasodilation, erythema and edema were blocked. Note that the photo was taken six weeks after injection. This phenomenon could be consistently reproduced after each injection cycle, and has been observed in additional patients.

After the effect dissipated in 20 weeks, another injection was given in similar locations. The same protected geometric area was again in evidence within 48 hours after botulinum toxin administration.

Case II

A 44-year old woman with interest in having glabellar lines reduced with botulinum toxin experienced generally facial flushing and swelling sometimes associated with headache following extreme exertion. After regional botulinum toxin was administered at a dose of 5 units, an area with diameter measuring 25 mm around the injection sites was protected from the flushing and abnormal sensory effect associated with such exertion. She noted this protective effect lasted 10-14 weeks.

Figure 2:
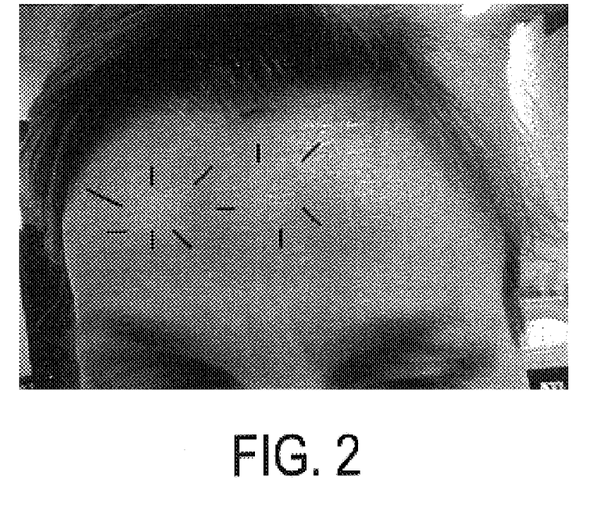
FIG. 2 is a photograph of the result after three days of injecting a patient suffering from heat release, vasodilatation, erythema, and edema with a chemodenervating agent, showing the protective anti-inflammatory effect of the chemodenervating agent, which effect has been noted in less than 24 hours after injection and prior to development of any weakness, indicating novel dose and pharmacological response for the subject anti-inflammatory bioeffect.
Figure 3A:
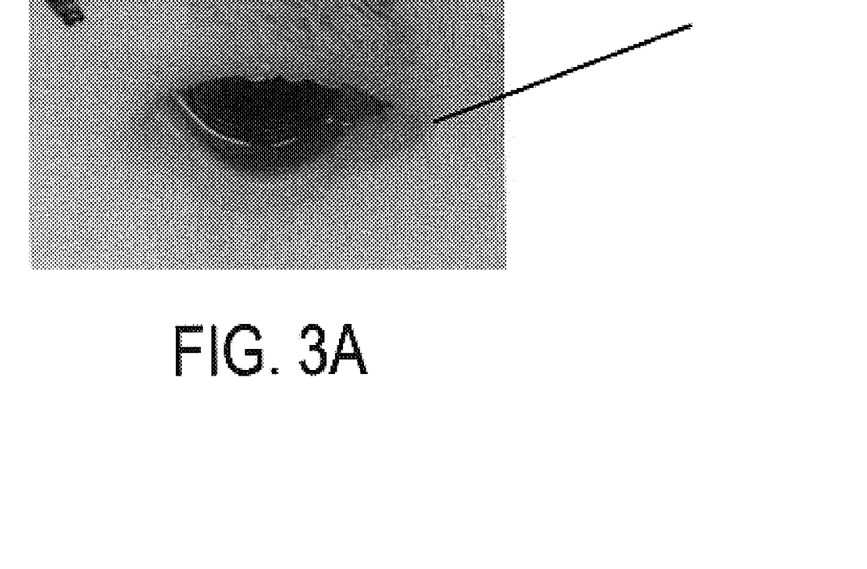
FIG. 3A is a photograph showing the ocular surface of an animal exposed to an aerosol containing ragweed pollen which induced ocular allergic conjunctivitis resulting in edema and erythema, as well as scratching behavior of the animal.
Figure 3B:
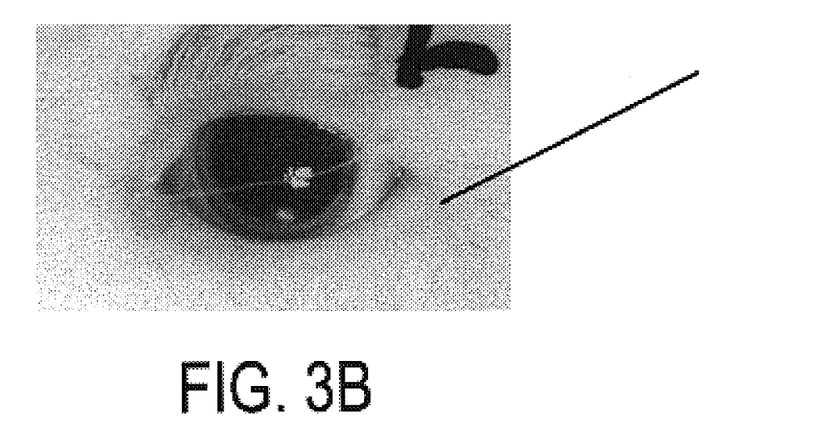
FIG. 3B is a photograph of the ocular surface of the animal eyes of the animal of FIG. 3A indicating the results of having received epibulbar injection of the subject denervating agent, showing reduced edema and erythema.
Figure 4:
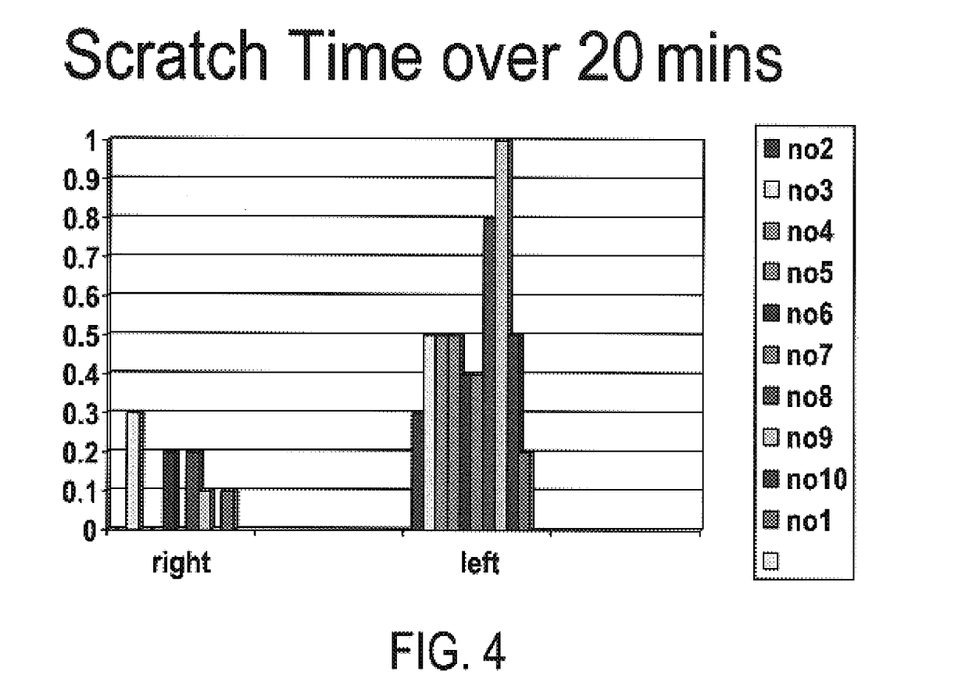
FIG. 4 is a graph of scratch time over 20 minutes in which scratching was markedly less in the injected versus the non-injected control eye.
Figure 5:
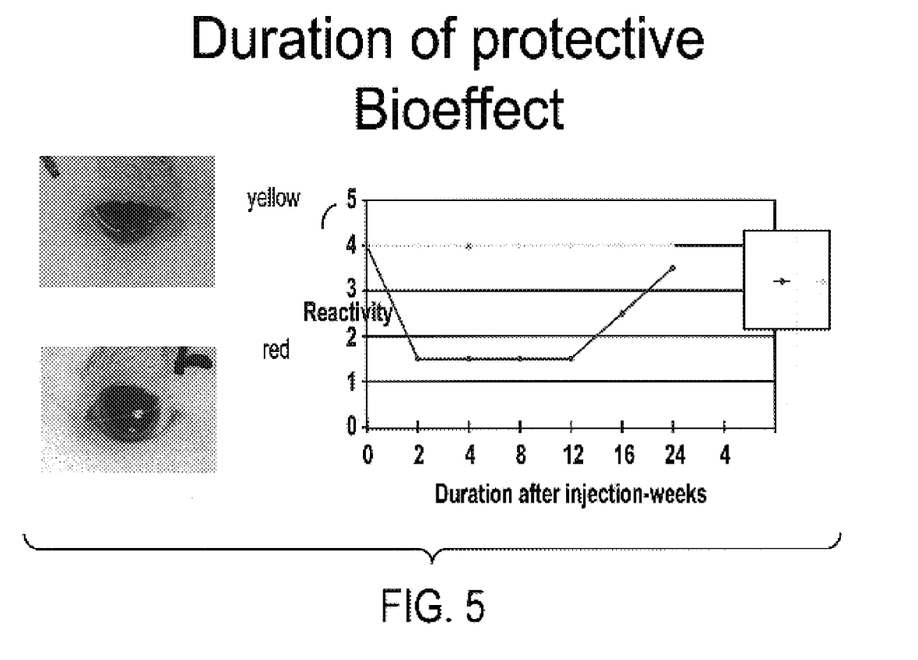
FIG. 5 is a graph illustrating the duration of protective effect for the administration of a denervating agent in the treatment of ocular conjunctivitis due to ragweed sensitization.
Figure 6:
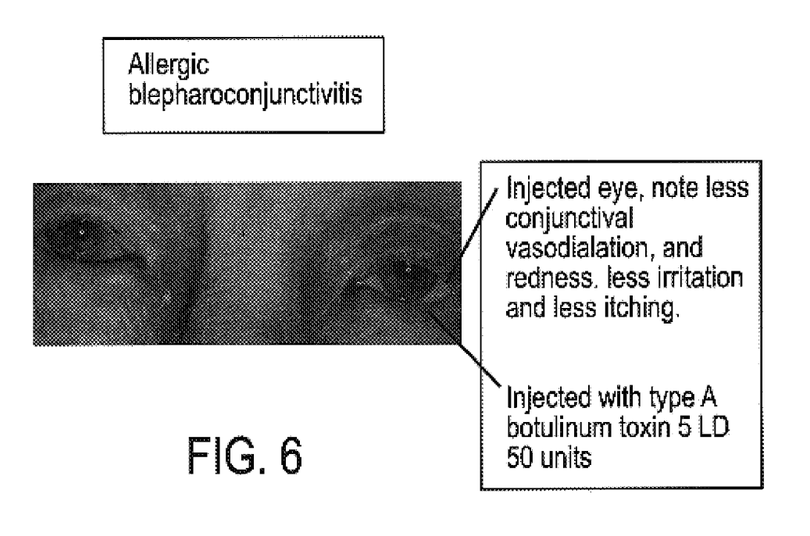
FIG. 6 is a photograph of a patient having severe atopic conjunctivitis, with the left eye treated with the subject chemodenervating agent, illustrating that after periocular injection of chemodenervating agents in low dose, conjunctival erythema, edema and symptomatic itching are substantially improved.
Figure 7A:
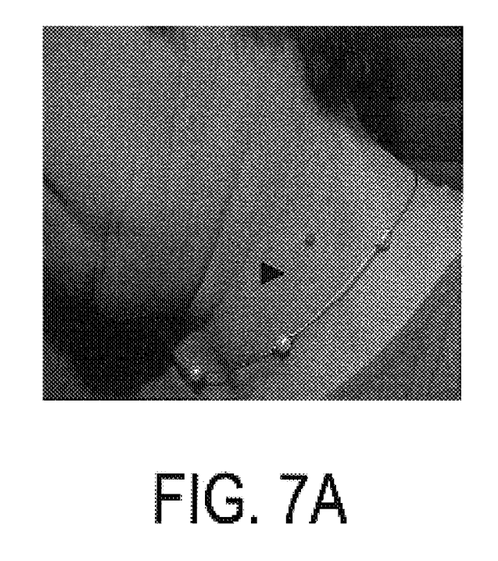
FIGS. 7A-D are a series of photographs of thermal evidence of deep tissue inflammation associated with adult onset spasmodic torticollis, with red patches appearing over points of maximal pain and tenderness, with such red spots, best detectable with thermal sensitive photographic film, never having been clinically described for this condition; and, FIGS. 8A and 8B are before and after photographs of the effect of the subject denervation agent on adult onset spasmodic torticollis at lower doses, <20 units, showing reduction of red discoloration associated with myositis associated with torticollis, indicating an area of surpressed erythema in the region of injection, corresponding to the known geometric field of diffusion for the given quantity of botulinum toxin injected.
Figure 7B:
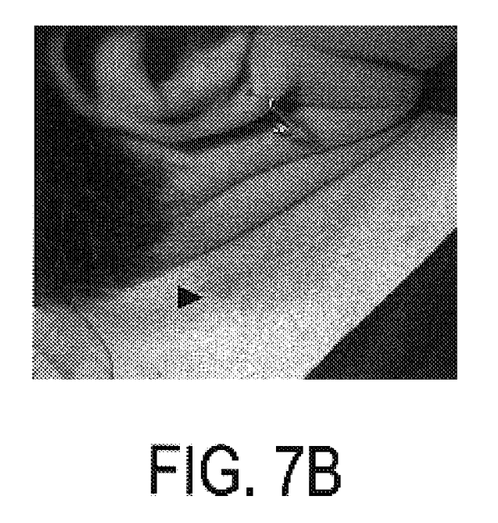
Figure 7C:
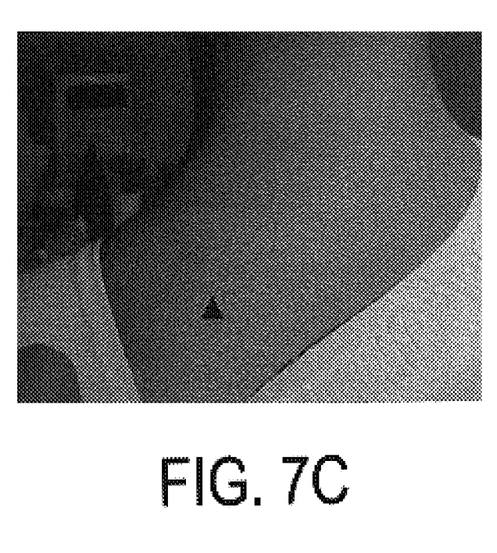
Figure 7D:
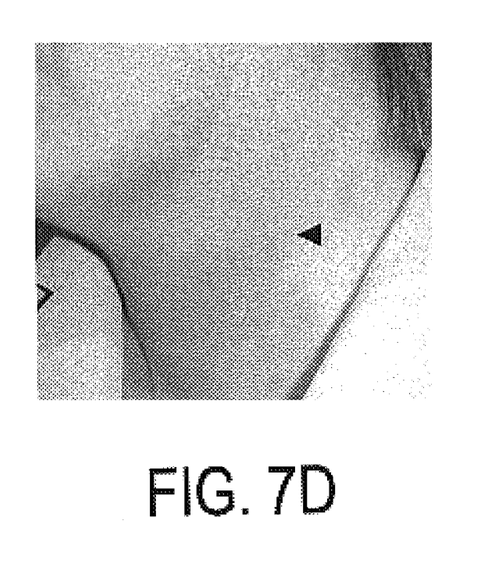

FIG. 2 is a photograph of this woman within three days after injection, showing the blocking effect on heat release, vasodilation, erythema and edema, which effect expands to its maximum in 12 days, and persists for at least four months.

Discussion

Urticaria refers to the formation of hives occurring usually in response to allergic reactions to pollens, foods, dander or other forms of antigens. The process often involves binding of allergens to the IgE receptor of the mast cell membrane bound IgE, causing release of preformed mediators such as histamine and serotonin as well as newly formed mediators from arachadonic acid such as prostaglandins and leukotrienes, platelet activating factor, kinoginase and tryptase, as well as cytokines. A late response can be seen after an allergic urticarial reaction which may be painful.

Urticaria may be provoked by non-allergens, including codeine, morphine, compound 48/80, synthetic ACTH, and anaphylatoxins C3a, C5a. Important, relative to the case observation, is the reactivity of mast cells to acetycholine as described by Fantozzi, R., Masini, E., Blandina, P., Mannaioni, P. F., Bani-Sacchi, T., Release of Histamine from Rat Mast Cells by Acetycholine, Nature (1978 Jun. 8) 273 (5662): 473-4.

Mast cells are known to be abundant around blood vessels in the scalp, orbit and lids, and are thought to be important in allergic conjunctivitis as described by Allensmith, M. R., Baird, R. S., Percentage of Degranulated Mast Cells in Vernal and Giant Papillary Conjunctivitis, Am J. Opthalmol, 9, 71-75, 1981, and Henriquez, A. S., Kenyon, K. R., Allansmith, M. R. Mast Cell Ultrastructure, Comparison in Contact Lens-associates Giant Papillary Conjunctivitis and Vernal Conjunctivitis, Arch Opthalmol 99:1266-1272, 1981. Mast cells reactivity has been associated with hayfever bepharoconjunctivitis, asthma, allergic rhinnitis, and allergic forms of eczema. Mast cells are also seen abundantly in inflammatory responses in rheumatoid arthritis and inflammatory bowel disease.

Mast cells are closely associated with Type 1 hypersensitivity reactions. In such reactions, the typical response involves sensitization with an antigen, formation of immunoglobulin, IgE class, binding of immunoglobulin to the external cell membrane by its FcE receptor, and setting the stage for hypersensitivity to the second exposure to the antigen. Upon second exposure, IgE reacts with the antigen effect in a degranulation response of the mast cell, in which there is a release of preformed mediators such as histamine and serotonin, platelet activating factor, and newly formed mediators such as leukotrienes, prostaglandins, tryptase, kininogenase which effect vasodilatation, vascular permeability, microthrombi, edema, mucous secretion. The response persists manifesting a late response after 8 hours. The late response is associated with pain as described by Roit, I., Brostoff, J., Male, D., Immunology $5^{th}$ Edition Mosby, 1998.

Conjunctivitis

Experiments were conducted on the effects of chemodenervation on the biologic reactivity of mast cells on the Guinea Pig Conjuctiva. In order to test the viability of using chemodenervating agents as a method of reducing the inflammatory response associated with hypersensitivity, an animal model consisting of sensitization of Hartley Guinea Pig Conjunctiva to short ragweed pollen, eg Ambrosia Artemisiaefolia, was used. This animal model of ocular allergy involves exposing the nasal and conjunctival mucosae to topical ragweed pollen, followed by subsequent challenge. After challenge, these animals develop an acute hypersensitivity reaction within 2-3 minutes which strongly resembles clinical hayfever conjunctivitis and represents a rapid inflammatory response. Histology evaluation of this animals model from exenterated orbis indicated marked infiltration of eosinophiles, as well as strong evidence of mast cell degranulation as described by Merayo-Lloves, J., Calonge, M., Foster, C. S., Experiential Model of Allergic Conjunctivitis to Ragweed in Guinea Pig, Current Eye Research 14:487-494, 1995.

Each animal was sensitized by spraying spores of ragweed pollen into the conjunctiva and nasal cavities for two weeks at a quantity of 2.5 mg per exposure. After two weeks, the animals demonstrated the conventional signs of acute hypersensitivity within several minutes after, exposure, including edema, erythema, microvascular thrombi, mucous exudation, and irritation as demonstrated by animals scratching behavior.

After hypersensitivity was established using this animal model, the left eye of each test animal was injected with 0.675 mouse units of botulinum toxin Type A, the preferred chemodenervating unit within the peribulbar area.

Appropriate anti-inflammatory effect was monitored by two observations within the animal model:

1. Edema.
2. Erythema.
3. Behavior changes in animals measured by scratch limb rubbing time 15 minutes after exposure to the ragweed.

The protective effect of the eye injection with the chemodenervating agent could be demonstrated within one week with respect to animals behavior, as well as observed edema and erythema comparing the test eye to the contra lateral eye not injected. This effect appeared most prominent within the first 10 minutes of the inflammatory exposure with allergen to the sensitized ocular surface and lasts up to six months.

Specifically, and as shown in FIG. 3, the animal was exposed to an aerosol containing ragweed pollen which initially had no inflammatory effects on the ocular surface. After 10 days of exposure to the antigen, the guinea pigs ocular response converted to a rapid onset of edema, conjunctival vascular dilation, microhemmorphages, and scratching behavior. As can be seen in FIG. 4, the eye which received the epibulbar injection after being sensitized shows reduced edema and erythema, with the duration of the effect being 4-5 months.

As shown in the bar graph of FIG. 5A, animals injected with botulinum toxin scratch significantly less often, with FIG. 5B being a graph showing protection up to six months.

Allergic Blepharoconjunctivitis

Four patients experiencing severe conjunctival and lid margin erythema, itching and ocular mucous discharge associated with ocular irritation were tested. Each patient had been treated with conventional therapy, including anti-histamine eyedrops, steroid drops, and sympathomimetic ocular preparations without relief in symptoms. Because of unrelenting symptoms, the subject anti-inflammatory agent was offered as an "off label" use in an attempt to alleviate their distressing affliction. As BOTOX-™ from Allergan is the only denervating pharmaceutical currently available for use in ocular movement disorders, BOTOX-™ was injected into the periocular region close to the lid margin in each patient, using dose injection doses less than 5 LD 50 units per injection site to limit undesirable diffusion. Subsequently, each patient was followed up after 4-7 days. Each patient noticed improvement in irritation, itching, erythema and general discomfort associated with their condition.

As shown in FIG. 6, a patient demonstrating severe atopic conjunctivitis for four months had his left eye treated 48 hours prior to the photograph. After periocular injection in a low dose of 5LD 50 units, injected eye lids showed vasodilation, redgress and irritation.

Blepharospasm

A visual analogue evaluation of 20 patients with essential blepharospasm were compared with a 10 patient control population. The essential blepharospasm patient clearly had statistically significant differences with respect to light sensitivity compared to controls in which $p<0.05$ using the visual analogue scale. 15 units of botulinum toxin were administered to each periorbital area. The effect of botulinum toxin on photophobia was evaluated using the visual analogue scale pre-injection and 2-3 weeks after injection in an open label study. In a series of 14 patients, the effects on photophobia were reported to be significantly mitigated ($p<0.05$). Here, the anti-inflammatory mechanism of the subject agent is clearly active.

Treatment of Internal Inflamatory Diseases

In the past, it was thought that the tissue mechanisms associated with using chemodenervating agents have solely involved the use of botulinum toxin as a means of causing muscle relaxation or to produce certain autonomic effects blocking decreased sweating. Although there have been conditions treated by chemodenervating agents which have had associated inflammatory reaction as a part of the clinical syndrome, the concept of muscle relaxation induced by such agents has been thought to be the mechanism by which such agents induce the beneficial effects. It has now been found that the subject agent has useful anti-inflammatory properties capable of blocking ocular surface allergic inflammation in man and animal models, as well as generalized inflammation within the denervation field created.

For treatment, the practitioner defines a fixed anatomic area in which symptomatic and/or destructive inflammatory processes are occurring. Knowledgeable of dose related diffusion properties and potency of the preparation being used, the practitioner defines the anatomic area to be treated. Avoiding critical structures, e.g. blood vessels, nerves and anatomic cavities, the practitioner injects a fixed dosage of the chemodenervating agent so as to create a denervation field, reducing the intensity of tissue destruction occurring within the area of treatment. Such a field can be defined internally, e.g. stomach mucosae-gastrits, joint-arthritis and muscle myositis. Follow-up involves monitoring for the cardinal sign of inflammation-pain redness, edema and discharge. Adjuvant therapy with other anti-inflammatory agents would be contemplated.

Spasmodic Torticollis

Spasmodic torticollis, eg. Cervical dystonia, regional and segmental dystonia of neck, was first treated with botulinum toxin in 1984. The condition involves involuntary movements, postures and tremors of the head and neck region often associated with pain. Muscle hypertrophy and neck rigidity are often associated components of the syndrome. The condition often occurs in mid-life, and generally is chronic with occasional remissions. Heredity and genetic etiology has been implicated, as patients often have other family members afflicted with similar conditions as described by Borodic, G. E., Joseph, M., Fay, L., Cozzolino, D., Ferrante, R., Botulinum A Toxin For The Treatment Of Spasmodic Torticollis, Dysphagia And Regional Toxin Spread. Head & Neck 12:392-398, 1990, Borodic, G. E., Mills, L., Joseph, M. Botulinum A Toxin For Adult Onset Spasmodic Torticollis, Plastic And Reconstructive Surgery 87:2, 285-289, 1991. The cause of this condition has been attributed in the past to direct derangement within the central nervous system, as patients have been noted to have abnormal eye movement patterns and auditory and other sensory brainstem-evoked measurements, as reported by Drake, M. E., Jr., Brian-Stem Auditory-Evoked Potentials In Spasmodic Torticollis Arch, Neural 1988 February; 45(2):174-5. However, convincing evidence has been lacking, as discussed by Horner, J., Riski, J. E., Weber, B. A., Nashold, B. S., Jr. Swallowing, Speech, And Brainstem Auditory-Evoked Potentials In Spasmodic Torticollis, Dysphagia 1993; 8(1):29-34.

Regional and segmental dystonias have been associated with atypical patterns of brain metabolism when measured with PET scanning, as described by Becker, G., et al, Comparison Of Transcranial Sonography, Magnetic Resonance Imaging, And Single Photon Emission Computed Tomography Findings In Idiopathic Spasmodic Torticollis, Mov Disord 1997 January; 12(1):79-88.

As illustrated in FIGS. 7A-D, it has been discovered and is a part of the subject invention that an important clinical sign, not previously described in the medical literature, is associated with the syndrome. This sign involves the formation of red patches noted on the skin, often associated with painful areas, best demonstrated with red wavelength sensitive photography. Here, four patients with cervical dystonia were diagnosed with red patches. This sign involves the formation of red patches noted on the skin often associated with painful areas. These areas are generally warmer to touch, and not associated with any intrinsic skin changes such as scaling, crusting or any signs of cutaneous inflammation or cell proliferation. It has been found that these changes are more prominent in patients with cervical dystonia who are having more difficulty with pain. These patches typically occur posterior to the scalene muscle and inferior to the ear, although they have been seen over the trapezius and sternomastoid muscle. The red patch has been found to represent an area of maximal tenderness, and provides evidence that inflammation is an integral component of the spasmodic torticollis syndrome. Moreover, the red patch indicates that spasms inherent in the torticollis syndrome are driven at least in part by the inflammatory process, and that pain occurring in torticollis is, in part, inflammatory in nature. Additionally, the red patch indicates that inflammation in torticollis in peripheral tissues may be neurogenically mediated, and that proprioceptive information to the brain leaving muscles is to some degree mediated by elements of neurogenically provoked inflammation or inflammation associated autocoids.

Figure 8A:
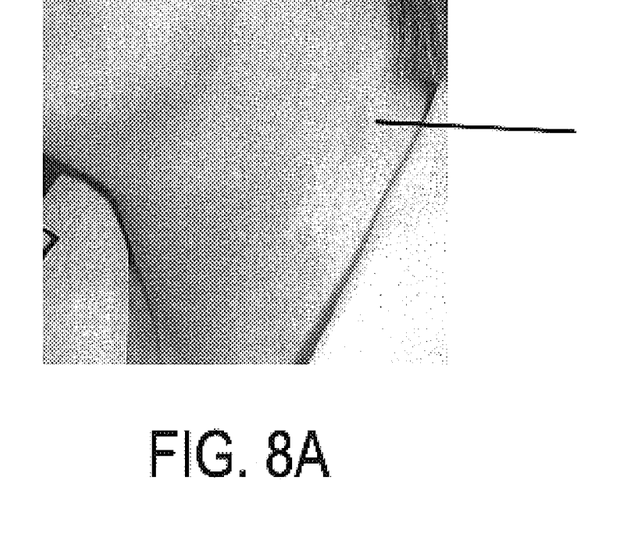
Figure 8B:
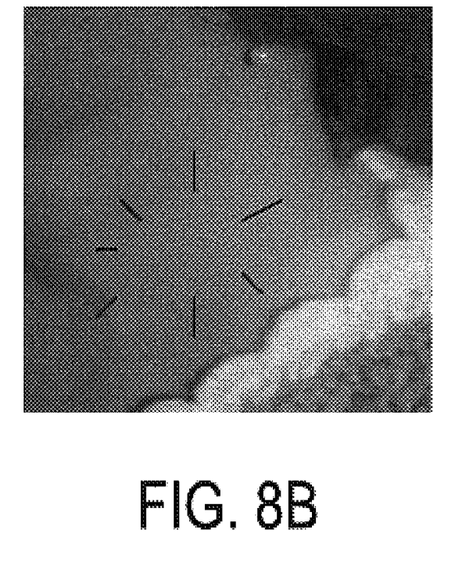

Botulinum toxin injected into red areas noted to be painful and thermally active in accordance with the subject invention has been demonstrated to block the erythema, pain, increased tenderness, and heat loss within the area consistent with the denervation diffusion potential for the given dose, as can be seen in FIGS. 8A and 8B, in which FIG. 8A shows the red patch and FIG. 8B shows a blanched area of blocked inflammation at the injection site. Minimum doses range between 0.6 units to 15 units and are far lower than that required to produce regional weakness. This finding points to and further demonstrates the anti-inflammatory effect of botulinum toxin on deeper muscular tissues which are demonstrating cardinal signs of inflammation at the body's surface, namely, pain, erythema, tenderness, increased heat loss, and spasm.

Rheumatoid Arthritis

One of the most devastating chronic internal inflammatory diseases is rheumatoid arthritis, characterized by joint and periocular involvement and chronic inflammation causing destruction of cartilage and ligamentous structures involving joints throughout the body. Immunologic causes have been cited as the underlying pathologic mechanism of the chronic destructive process, and mast cells have been noted in large quantities within the tissue pannus surrounding joints afflicted. Edema, joint effusions, stiffness, spasms, pain, and erythema, are all components of the arthritis involved regions. Multiple anti-inflammatory agents have been tried, with variable results to suppress the destructive effects of this systemic disease on bone and joints.

The invention described herein offers a means of localized application of an anti-inflammatory agent which is injected directly into joints or periarticular muscular tissues which creates an effect on the rapid inflammatory response and peripheral neural elements governing the inflammatory response. The dose is quantified using the LD 50 to limit diffusion away from the injected area. The application may be repeated at 3-month intervals and at titrated doses by clinical methods so as to limit any weakness within the injected region.

The Experimental Model

The animals model and clinical examples described herein were used to test the various botulinum toxins for this anti-inflammatory bioeffect.

The fundamental clinical properties associated with and characterizing inflammation are
1. pain or altered sensation
2. erythema (redness)
3. edema
4. heat
5. muscular reactivity (often spasm)

General Test Results

In patients tested having exertion urticaria, spasmodic torticollis, Type I hypersensitivity, pollen induced conjunctivitis, allergic blepharoconjunctivitis, there has been:
1. Repeated improvement in erythema within the denervation filed
2. Improvement in sensation, pain and or itching within the denervation field
3. Improvement in edema formation within the denervation field
4. Differential in apparent heat release within the denervation field
5. Relaxation of human muscle spasms within the denervation field.

Mechanisms of Clinical Action of Botulinum Toxin

The rational for the treatment for dystonia with botulinum toxin is that regional dose dependent weakening of the abnormally hyperactive muscles with botulinum toxin should lead to clinical improvement. Botulinum toxin is known to cause a form of reversible denervation atrophy, which is reversible in 3-4 months. The process of pre-axonal terminal sprouting with spread of acetylcholine receptors and cholinesterase has been well characterized by Duchenne and subsequently many others. In most if not all applications, weakness of injected muscles is easily assessed, and such as limb dystonia, improvement is not generally seen without detectable weakness.

Notwithstanding the well-known effects at the neuromuscular junction and muscular weakness which ensues, many clinicians who treat regional movement disease with botulinum toxin have questioned whether there may be a clinical effect of the toxin beyond mere weakening of the muscles. The reasons for this view are as follows:

The beneficial effects may not occur in parallel with the weakness; often there is a latency period of up to 2 weeks before a benefit is observed, whereas the weakness developed within a few days. The opposite is also a common experience, where patients report a response within a few hours or even shorter. A placebo effect is often suspected here. The duration of response may outlast the weakness so that the benefit continues after strength has recovered. The degree of benefit may seem much greater than expected from the degree of weakness. There may be clinical benefit from muscles quite remote from the original denervation field and sites of injection.

For example, injections into orbicularis oculi for blepharospasm may reduce dystonic movements of the lower face and jaw, not due to spread of the toxin. In writer's cramp, dystonic posturing of proximal muscles or "overflow phenomenon" frequently improves after injection of distal muscles. Photophobia is an important component of essential blepharospasm syndrome, and is often improved after botulinum toxin injections.

Instead, improvement occurs often at doses less than necessary to produce substantial weakness such as 15 units per lid. Because of weakness created by botulinum toxin and possible dry eye syndrome and keratitis that can result, photophobia should be worse after botulinum toxin injections. The suppression of photophobia is counterintuitive, but may be explained by the subject bioeffect.

These observations may be explained by a direct or indirect central effect of the toxin. It is well-known that radioactivity after injection of labeled botulinum toxin into a muscle can be tracked back into the spinal cord, suggesting retrograde axonal transport as described by Weignad, H., Erdmann, G., Weillhoner, H. I., Labeled Botulinum A Neurotoxin: Pharmacokinetics In Cats After Intramuscular Injection, Naunyn Schmeidbergs Arch Pharmacol 1976: 292:161-165. It is not known whether this activity represents the label itself or the presence of the toxin in whole or part within the cord. The influence of this phenomenon on the mechanism of botulinum toxin however, is at best conjectural.

Although direct central effects of the toxin could explain some of these findings, it is also possible that they are secondary to a peripheral action, such as an effect on muscle spindle afferents or efferents. To date there is no conclusive evidence of direct central activity in the toxin. PET studies of patients with writer's cramp have shown some motor cortex re-organization after treatment, possibly as a result of denervation, but did not affect the abnormal pattern of cortical dysfunction. Additionally, pain relief, often the most sensitive component to the beneficial effects of botulinum toxin, is often out-of-proportion to weakness created by the injections.

New Bioeffect

The above observations lend credence to second receptors within injected tissue remote from the neuromuscular junction. The subject invention has been found to rest on a new bioeffect on release of mediators within the denervation field created by a point injection of botulinum toxin which have an onset of effect much shorter than the neuromuscular weakening effect. The above offers an explanation as to why beneficial effects are out of proportion to weaknesses created, and explains different dose response relationships among the various immunotypes of botulinum toxin.

Application for the treatment of blepharospasm, photophobia and its mitigation are previously unrecognized bioeffects of botulinum toxin.

Having now described a few embodiments of the invention, and some modifications and variations thereto, it should be apparent to those skilled in the art that the foregoing is merely illustrative and not limiting, having been presented by the way of example only. Numerous modifications and other embodiments are within the scope of one of ordinary skill in the art and are contemplated as falling within the scope of the invention as limited only by the appended claims and equivalents thereto.

What is claimed is:
1. A method of reducing inflammation, comprising the step of administering a therapeutically effective dose of a botulinum toxin to an affected area of a subject suffering from inflammation, wherein the botulinum toxin reduces at least one symptom of inflammation, and wherein said therapeutically effective dose is sufficient to reduce said at least one symptom of inflammation but less than a dose necessary to produce substantial muscle weakness within the affected area.

2. The method of claim 1, wherein the chemodenervating agent is selected from the group consisting of botulinum toxin types A, B, C, D, E, F, and G.

3. The method of claim 1, wherein the chemodenervating agent is administered in conjunction with another anti-inflammatory agent.

4. The method of claim 3, wherein the other anti-inflammatory agent is a steroid.

5. The method of claim 3, wherein the other agent is non-steroidal.

6. A method for treating allergic blepharoconjunctivitis comprising the step of administering a therapeutically effective dose of a botulinum toxin in a periocular area of a subject suffering from blepharoconjunctivitis, thereby reducing inflammation, wherein said therapeutically effective dose is sufficient to reduce at least one symptom of inflammation but less than a dose necessary to produce substantial muscle weakness within said periocular area.

7. A method for treating classic type 1 hypersensitivity comprising the step of administering a botulinum toxin to an affected area of a subject suffering from classic type 1 hypersensitivity, thereby reducing inflammation, wherein said therapeutically effective dose is sufficient to reduce at least one symptom of inflammation but less than a dose necessary to produce substantial muscle weakness within said affected area.

8. The method of claim 7, wherein the hypersensitivity is hay fever, rhinitis, allergic rhinitis, allergic forms of eczema, urticaria, rheumatoid arthritis, inflammatory bowel disease, or asthma.

9. A method for treating inflammation, comprising the step of administering a botulinum toxin to an affected area of a subject suffering from inflammation in a therapeutically effective dose sufficient to reduce a rapid-phase inflammatory response under neural regulation, thereby reducing at least one symptom of inflammation, and wherein said therapeutically effective dose is sufficient to reduce the at least one symptom of inflammation but less than a dose necessary to produce substantial muscle weakness within said affected area.

10. The method of claim 9, wherein the botulinum toxin is selected from the group consisting of botulinum toxin A, B, C, D, E, F and G.

11. The method of claim 6, wherein the chemodenervating agent is selected from the group consisting of botulinum toxin types A, B, C, D, E, F, and G.

12. The method of claim 7, wherein the chemodenervating agent is selected from the group consisting of botulinum toxins toxin types A, B, C, D, E, F, and G.

13. The method of claim 9, wherein said botulinum toxin reduces mast cell degranulation, thereby reducing inflammation.

14. The method of claim 13, wherein the mast cell is activated by either non-immunologic or immunologic-based processes.

15. The method of claim 9, wherein the therapeutically effective dose is sufficient to reduce release of preformed mediators of inflammation.

16. The method of claim 15, wherein the therapeutically effective dose is sufficient to reduce release of leukotrienes, prostaglandins, histamine, serotonin, platelet activating factor, tryptase, or kininogenase.

17. The method of claim 1, wherein said inflammation is ocular surface allergic inflammation.

18. The method of claim 9, wherein the therapeutically effective dose is between one third and several orders of magnitude less than the dose necessary to produce substantial muscle weakness in an affected area.

19. The method of claim 6, wherein the therapeutically effective dose is between one third and several orders of magnitude less than the dose necessary to produce substantial muscle weakness in an affected area.

20. The method of claim 7, wherein the therapeutically effective dose is between one third and several orders of magnitude less than the dose necessary to produce substantial weakness in an affected area.

21. The method of claim 1, wherein the at least one symptom of inflammation is heat release, vasodilation, erythema, edema or pain.

22. The method of claim 21, wherein the at least one symptom of inflammation is pain.

23. The method of claim 9, wherein the at least one symptom of inflammation is heat release, vasodilation, erythema, edema or pain.

24. The method of claim 23, wherein the at least one symptom of inflammation is pain.

* * * * *